(12) United States Patent
Liu et al.

(10) Patent No.: US 11,376,149 B2
(45) Date of Patent: Jul. 5, 2022

(54) PATCH WITH EXPANSION SUPPORT EFFECT

(71) Applicant: RIBCURE CO., LTD., Taichung (TW)

(72) Inventors: Chun-Sung Liu, Taichung (TW); Ying-Chieh Su, Tainan (TW)

(73) Assignee: RIBCURE CO., LTD., Taichung (TW)

( * ) Notice: Subject to any disclaimer, the term of this patent is extended or adjusted under 35 U.S.C. 154(b) by 306 days.

(21) Appl. No.: 16/757,619

(22) PCT Filed: Oct. 23, 2017

(86) PCT No.: PCT/CN2017/107278
§ 371 (c)(1),
(2) Date: Apr. 20, 2020

(87) PCT Pub. No.: WO2019/079924
PCT Pub. Date: May 2, 2019

(65) Prior Publication Data
US 2020/0337876 A1    Oct. 29, 2020

(51) Int. Cl.
*A61F 5/03*    (2006.01)
(52) U.S. Cl.
CPC ..................... *A61F 5/03* (2013.01)
(58) Field of Classification Search
CPC .. A61F 5/03; A61F 13/00; A61F 2013/00165; A61F 2013/00089;
(Continued)

(56) References Cited

U.S. PATENT DOCUMENTS

| 3,971,384 A * | 7/1976 | Hasson ............... A61B 17/085 |
| | | 606/218 |
| 7,198,609 B2 * | 4/2007 | Rolnick ................... A61F 5/03 |
| | | 602/5 |

(Continued)

FOREIGN PATENT DOCUMENTS

| CM | 203647402 U | 6/2014 |
| CN | 202933101 U | 5/2013 |
| CN | 103892877 A | 7/2014 |

*Primary Examiner* — Tarla R Patel
(74) *Attorney, Agent, or Firm* — Alan D. Kamrath; Karin L. Williams; Mayer & Williams PC (57) ABSTRACT

A patch having expansion and supporting effects, comprising a body (10, 10A, 10B), at least one first support member (20, 20A, 20B), and at least one second support member (30, 30A, 0B). The body (10, 10A, 10B) is provided with an adhesive surface (11, 11A) and a bonding surface (12, 12A, 12B); the two support members (20, 20A, 20B, 30, 30A, 30B) are provided on the body (10, 10A, 10B) and arranged to movably match each other; each support member (20, 20A, 20B, 30, 30A, 30B) is disposed in a length direction of the body (10, 10A, 10B) and provided with a fixing portion (21, 31, 21A, 31A, 21B, 31B), a snap-fit portion (22, 32, 22A, 32A), and a movable portion (23, 33, 23A, 33A, 23B, 33B), so that the two support members (20, 20A, 20B, 30, 30A, 30B) are disposed in the length direction of the body (10, 10A, 10B) and arranged linearly; the snap-fit portion (22, 32, 22A, 32A) of each support member (20, 20A, 20B, 30, 30A, 30B) is capable of being snap-fitted to the movable portion (23, 33, 23A, 33A, 23B, 33B) of the other support member (20, 20A, 20B, 30, 30A, 30B), and then a support strength required by the body (10, 10A, 10B) during an expansion process is provided by means of a structural pattern in which the snap-fit portion (22, 32, 22A, 32A) is snap-fitted to the movable portion (23, 33, 23A, 33A, 23B, 33B). Therefore, a patch that is simple in structure and (Continued)

convenient to use and has expansion and supporting effects is provided.

16 Claims, 10 Drawing Sheets

(58) Field of Classification Search
CPC .. A61F 2013/00217; A61F 2013/00387; A61F 2013/00455; A61F 2013/0054; A61F 2013/00825; A61F 13/0266; A61F 13/58; A61F 13/0269; A61F 13/0279; A61F 13/0283; A61F 13/0286; A61F 13/0289
See application file for complete search history.

(56) References Cited

U.S. PATENT DOCUMENTS

| | | | |
|---|---|---|---|
| 9,271,730 B2 * | 3/2016 | Fleischmann | A61B 17/08 |
| 9,757,131 B2 * | 9/2017 | Sanders | A61B 17/085 |
| 10,399,755 B2 * | 9/2019 | Sanders | B65D 63/02 |
| 10,426,474 B2 * | 10/2019 | Christiansen | A61B 17/085 |
| 11,147,556 B2 * | 10/2021 | Nezu | A61B 17/085 |
| 2012/0226306 A1 * | 9/2012 | Jackson | A61F 13/0259 |
| | | | 606/201 |
| 2616/0361062 | 12/2016 | Sanders et al. | |
| 2017/0035422 A1 | 2/2017 | Belson et al. | |

* cited by examiner

PATCH WITH EXPANSION SUPPORT EFFECT

BACKGROUND OF THE INVENTION

1. Field of the Invention

The present invention relates to a medical article, and in particular to a patch with an expansion support effect that is traction-fixed in a stretched manner when a patient is suffering from chest trauma, chest wall contusion, rib fractures, or sacral chest extension.

2. Description of Related Art

According to medical statistics, 70% of patients suffer from chest contusion in traumatic events. At least 50% of the said patients are diagnosed with fractures of ribs. However, even those patients without definite fractures of ribs suffer from severe pain caused by inflammation of periosteum that covers the ribs. The pain of rib fractures mainly comes from the flexion, rotation, vibration and inhalation of the body. The muscle groups of the chest wall and intercostal muscles pull the periosteum attached to the ribs, or the rib periosteal is pulled when the rib fractures are moved relatively. The patient's pain mainly occurs when changing the posture when getting in and out of bed, or when the body cavity lifts up and shakes due to deep breathing and coughing. Therefore, how to reduce the pain of patients with fractured ribs, especially the pain during moving activities, coughing, and deep breathing is a very important topic and the key to reducing complications in patients with rib fractures.

Conventional treatment to ease the pain caused by fractures of ribs includes three orientations: medication, external fixation, and internal fixation. In the treatment of medication, combination of analgesic drugs and muscle relaxants is commonly applied to ease the pain of the patient suffering from rib fractures, to relax muscles adjacent to the broken rib, and to keep the muscle adjacent to the broken rib free from convulsion. The medication may provide pain relief for the patient at rest. However, the painkilling effect of the medication is quite limited for the patient during movement.

The treatment of external fixation is to ease the pain of the patient suffering from rib fractures by lowering the chance of the offset occurring between the broken parts of the rib or by fixing the muscles adjacent to the broken rib. The external fixation includes: pressing by bare hand, sling, figure-8 bandage, rib belt, rib protector vest, elastic therapeutic tape, and chest orthosis. The treatment of internal fixation is to fix the ribs by surgery. The pain caused by broken ribs lasts for approximately seven days. Receiving a rib fixing surgery, the wound will produce pain of different types and parts. The surgery for applying the internal fixation has to detach muscles attached to the ribs. For surgical fixation, the ribs to be fixed must be separated from the muscles first. A large wound must be cut and the muscles attached to the ribs must be cut off or separated. After the surgery, there will be huge scars, and the chest wall muscle strength will also significantly decrease, so the patient's acceptance is very low.

However, in the conventional treatments for rib fractures, whether a rib belt that is compressed inwardly, or an adhesive fixation method using an elastic therapeutic tape and chest orthosis, they all limit the degree of internal muscle activities by skin texture fixation. These fixation manners using contraction methods are obviously contrary to the physiological structure of the human body. Because muscles tend to shorten the distance, for patients with rib fractures, it is usually that the ribs have not been completely broken and the lengths of the ribs have not been reduced, or the ends of the ribs are misaligned due to the pulling of muscles. The above-mentioned conventional retractable rib supporting devices not only restrict the expansion of the chest cavity, making it difficult for patients to perform deep breathing and sputum, but also cause compression of the fractured parts of the ribs when the human body bends, rotates, vibrates, or inhales and lifts, and this may increase pain and violation of the purpose of reducing pain. There are also some problems such as increased materials, complex tailoring, high prices, and stuffy wear. In addition, the fixation of elastic therapeutic tape is limited to the tape and only can provide a contraction effect with low elastic contraction tension and poor support effect. Therefore, the degree of pain relief is limited. In view of this, the conventional equipments and devices for the treatment of pain in rib fracture patients need to be improved.

To overcome the shortcomings of the conventional fixation treatment, the present invention provides a patch with an expansion support effect to mitigate or obviate the aforementioned problems.

SUMMARY OF THE INVENTION

The main objective of the present invention is to provide a patch with an expansion support effect that is traction-fixed in a stretched manner when a patient is suffering from chest trauma, chest wall contusion, rib fractures, or sacral chest extension.

The patch with an expansion support effect in accordance with the present invention comprises a body, at least one first supporting element, and at least one second supporting element, the at least one first supporting element and the at least one second supporting element disposed on the body, and the at least one second supporting element being mutually active and set up with the at least one first supporting element;

wherein the body is an elongated sheet and has a length, two opposite ends, a bottom face, a top face, an adhesive surface, and a mounting surface, the adhesive surface and the mounting surface are respectively disposed on the bottom face and the top face of the body along a lengthwise direction of the body;

wherein the at least one first supporting element is disposed on the body along the lengthwise direction of the body and has a fixed segment, an engaging segment, and a movable segment, the fixed segment is disposed on the mounting surface of the body at one of the two opposite ends of the body along the lengthwise direction of the body, the engaging segment is connected to the fixed segment, and the movable segment is disposed on the mounting surface of the body away from the fixed segment;

wherein the at least one second supporting element is disposed on the body along the lengthwise direction of the body, aligns with the at least one first supporting element, and has a fixed segment disposed on the mounting surface of the body at the other one of the two opposite ends of the body along the lengthwise direction of the body, an engaging segment connected to the fixed segment of the at least one second supporting element, and a movable segment disposed on the mounting surface of the body away from the fixed segment of the at least one second supporting element; and the engaging segment of each one of the at least one first supporting element and the at least one second supporting element engages with the movable segment of the other one of the at least one first supporting element and the at least one second supporting element.

Furthermore, in the above-mentioned patch with an expansion support effect, the engaging segment of the at least one first supporting element has multiple engaging units, the movable segment of the at least one second supporting element has at least one stuck unit, and the at least one stuck unit of the movable segment of the at least one second supporting element engages with the engaging units of the engaging segment of the at least one first supporting element.

In addition, in the above-mentioned patch with an expansion support effect, the engaging segment of the at least one second supporting element has multiple engaging units, the movable segment of the at least one first supporting element has at least one stuck unit, and the at least one stuck unit of the movable segment of the at least one first supporting element engages with the engaging units of the engaging segment of the at least one second supporting element.

Further, in the above-mentioned patch with an expansion support effect, each engaging unit of each one of the at least one first supporting element and the at least one second supporting element is a one-way engaging tooth, the at least one stuck unit of each one of the at least one first supporting element and the at least one second supporting element is an engaging hole formed through the respective movable segment, and an engagement between the one-way engaging tooth and the engaging hole of the at least one first supporting element and the at least one second supporting element allows adjusting a distance between the at least one first supporting element and the at least one second supporting element.

Additionally, in the above-mentioned patch with an expansion support effect, the engaging segment of each one of the at least one first supporting element and the at least one second supporting element is a belt extending along the lengthwise direction of the body, and the movable segment of each one of the at least one first supporting element and the at least one second supporting element is securely disposed on an end of the engaging segment of the respective supporting element away from the fixed segment of the respective supporting element and is disposed above the mounting surface of the body.

Furthermore, in the above-mentioned patch with an expansion support effect, each one of the at least one first supporting element and the at least one second supporting element has multiple supporting segments securely disposed on the mounting surface of the body at spaced intervals between the fixed segment and the movable segment of the respective supporting element, and each supporting segment of each one of the at least one first supporting element and the at least one second supporting element is movably connected to the engaging segment of the respective supporting element to hold the engaging segment of the respective supporting element steadily disposed above the mounting surface of the body.

Furthermore, in the above-mentioned patch with an expansion support effect, each supporting segment has a through hole formed through the supporting segment to connect with the respective engaging unit.

In addition, in the above-mentioned patch with an expansion support effect, the patch has multiple first supporting elements disposed on the mounting surface of the body at spaced intervals along a width direction of the body, the patch has multiple second supporting elements disposed on the mounting surface of the body at spaced intervals along a width direction of the body, and each one of the multiple second supporting elements is connected to and aligns with a respective one of the multiple first supporting elements along the lengthwise direction of the body.

Further, in the above-mentioned patch with an expansion support effect, the engaging segment of the at least one first supporting element is a rail, and the engaging segment of the at least one second supporting element is a plate mounted with the rail to enable the at least one second supporting element to move with the at least one first supporting element.

Additionally, in the above-mentioned patch with an expansion support effect, the fixed segments of the at least one first supporting element and the at least one second supporting element are respectively disposed on the two opposite ends of the body along the lengthwise direction of the body, the movable segment of the at least one first supporting element is securely disposed on the mounting surface of the body adjacent to the fixed segment of the at least one second supporting element, and the movable segment of the at least one second supporting element is securely disposed on the mounting surface of the body adjacent to the fixed segment of the at least one first supporting element.

Additionally, in the above-mentioned patch with an expansion support effect, the multiple engaging units of each one of the at least one first supporting element and the at least one second supporting element are arranged into two rows at linearly spaced intervals on a top face of the respective engaging segment along the lengthwise direction of the body, the movable segment of each one of the at least one first supporting element and the at least one second supporting element is a frame with an opening facing up and has two arms extended to the top face of the respective engaging segment, and each arm has a stuck unit protruded from a bottom of the corresponding arm, and the stuck units on the two arms of the movable segment of each one of the at least one first supporting element and the at least one second supporting element engage with two of the engaging units of the corresponding engaging segment.

Additionally, in the above-mentioned patch with an expansion support effect, each engaging unit is an engaging recess formed in the top face of the corresponding engaging segment, and each stuck unit is an engaging bead.

Additionally, in the above-mentioned patch with an expansion support effect, the body has at least one receiving space formed on the mounting surface, the at least one first supporting element is disposed in the at least one receiving space of the body, the fixed segment, the movable segment, and the supporting segments of the at least one first supporting element abut the mounting surface of the body, the at least one second supporting element is disposed in the at least one receiving space of the body, and the fixed segment, the movable segment, and the supporting segments of the at least one second supporting element abut the mounting surface of the body.

Additionally, in the above-mentioned patch with an expansion support effect, the at least one receiving space of the body is formed on the mounting surface of the body by two covering sheets respectively disposed on the mounting surface at the two opposite ends of the body, each covering sheet has an opening, and the openings of the two covering sheets face to each other to form the at least one receiving space between the two covering sheets, the fixed segment of the at least one first supporting element is restricted by one of the covering sheets disposed on one of the two opposite ends of the body without exposed outside the body, and the fixed segment of the at least one second supporting element is restricted by the other one of the covering sheets disposed on the other one of the two opposite ends of the body without exposed outside the body.

In summary, when the patch with an expansion support effect of the present invention is used, at least two of the supporting elements are linearly arranged and moved with each other on the body, and the engagement is provided between the engaging units and the stuck units of each supporting element. Then the expanded and deformed bodies can be provided with certain support strengths by the engagements between the two supporting elements after the bodies are stretched and deformed by an external force, which not only simplifies the overall structural complexity and greatly reduces the required cost, but also cooperates with the elastic contraction tension of the body and the supporting force of the two supporting elements. It can effectively avoid the pain caused by the patient during the moving activities, so as to provide a patch with a simple structure, convenient use, and an expansion support effect Other objects, advantages, and novel features of the invention will become more apparent from the following detailed description when taken in conjunction with the accompanying drawings.

DETAILED DESCRIPTION OF PREFERRED EMBODIMENTS

To be able to learn more about the technical features and practical efficacy of the present invention, and to utilize the present invention in accordance with the specification, the detailed description of the preferred embodiment as shown in the drawings is disclosed as follows.

Figure 1:
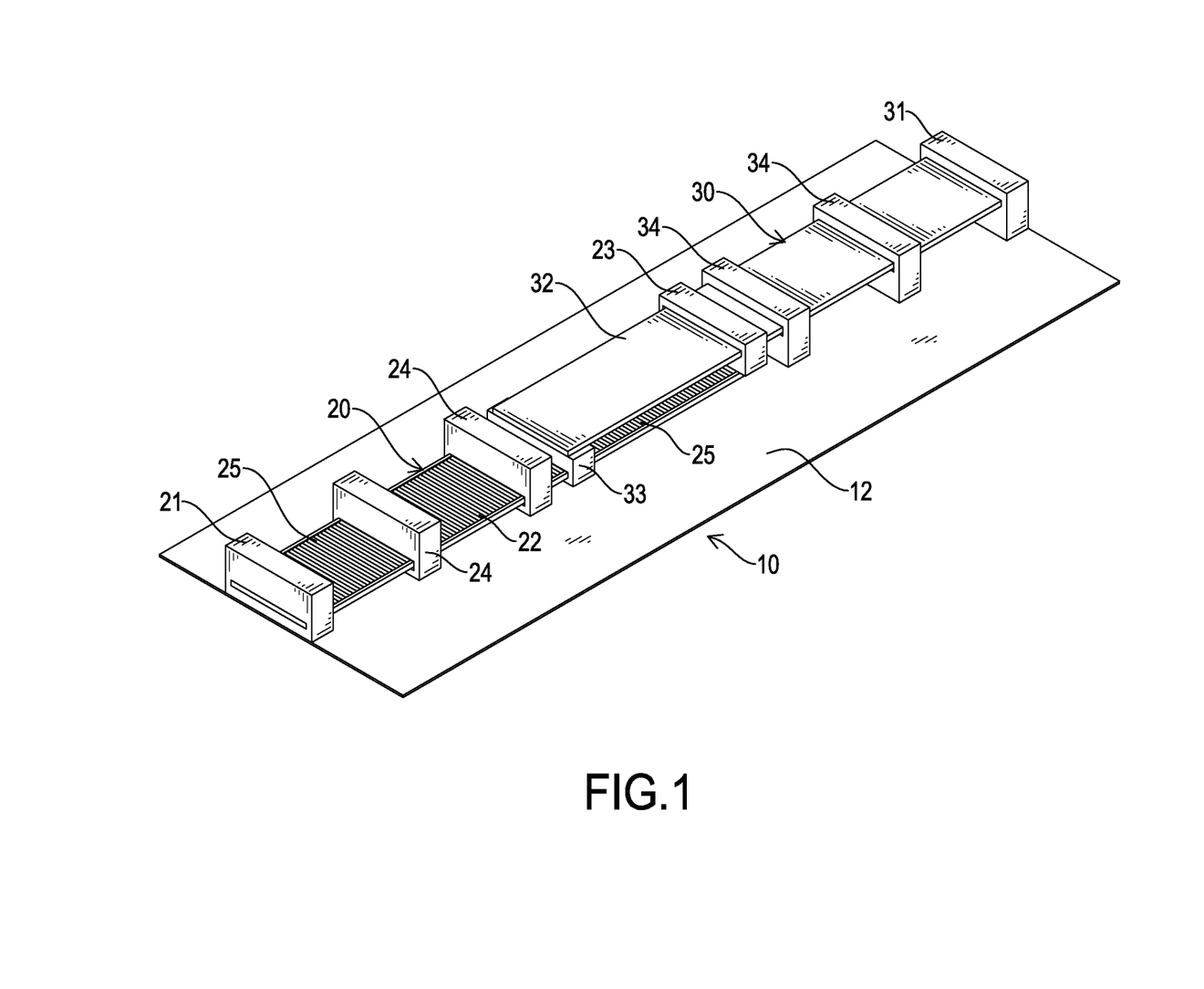
FIG. 1 is a perspective view of a first embodiment of a patch with an expansion support effect in accordance with the present invention.
Figure 2:
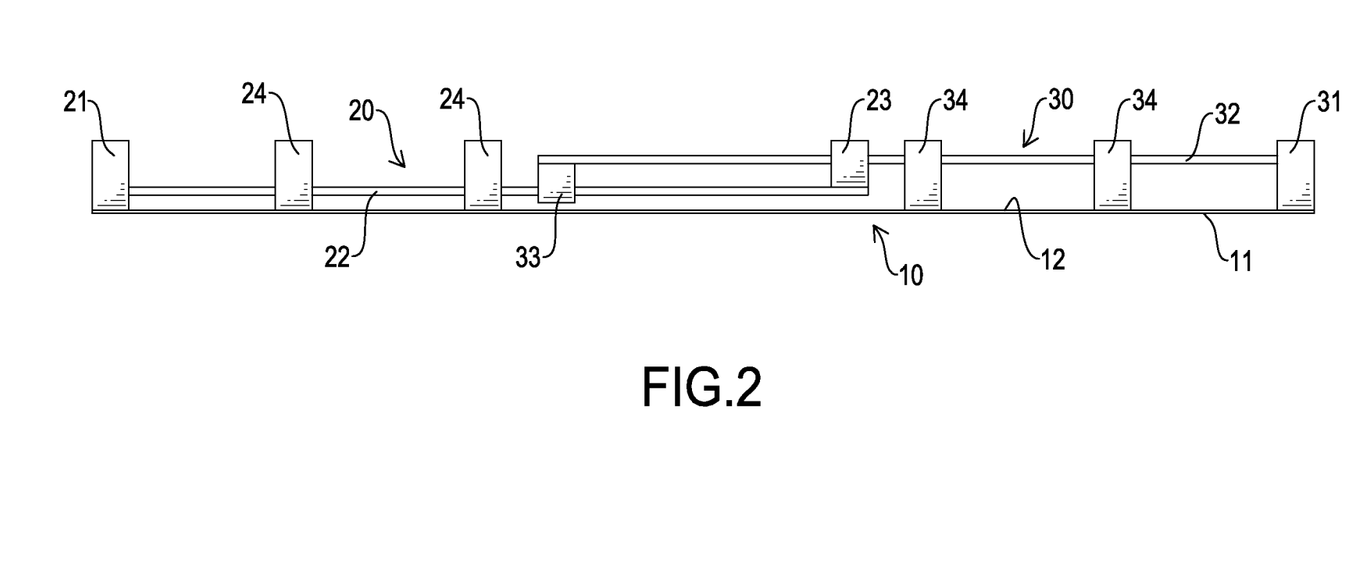
FIG. 2 is a side view of the patch with an expansion support effect in FIG. 1.
Figure 3:
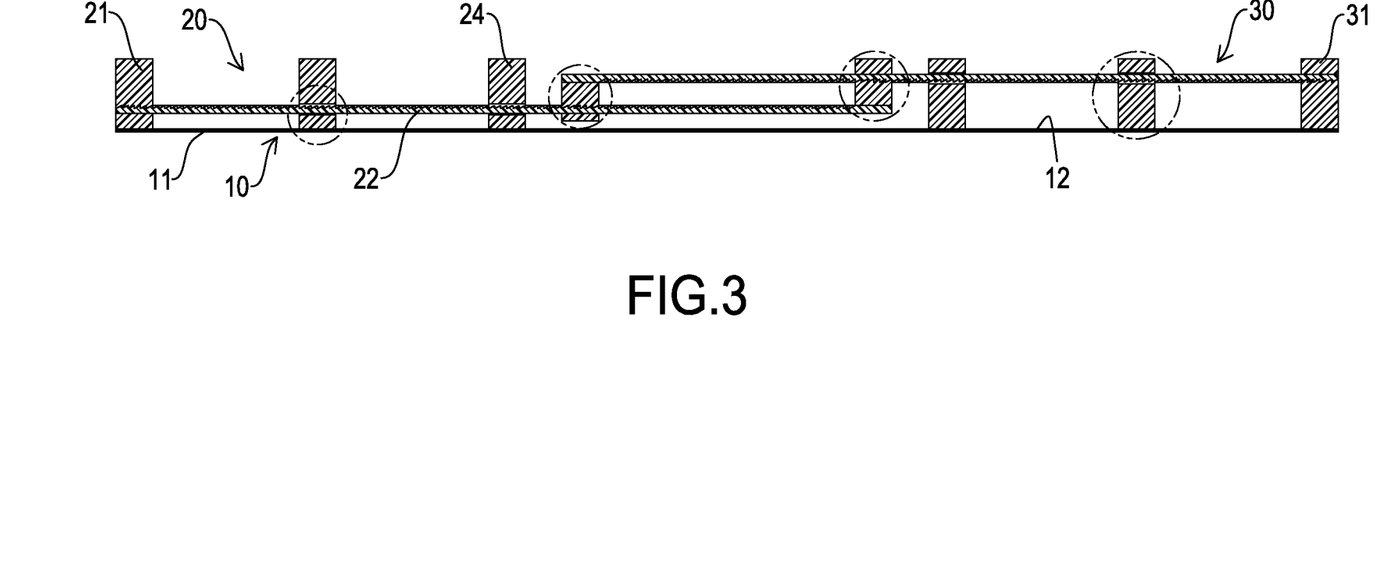
FIG. 3 is a cross-sectional side view of the patch with an expansion support effect in FIG. 1.

With reference to FIGS. 1 to 3, a first embodiment of a patch with an expansion support effect in accordance with the present invention has a body 10, at least one first supporting element 20, and at least one second supporting element 30. The at least one first supporting element 20 and the at least one second supporting element 30 are disposed on the body 10, and the at least one second supporting element 30 is mutually active and set up with the at least one first supporting element 20.

The body 10 is an elongated sheet, and the sheet may be made of various suitable materials such as non-woven fabric, gauze, bandage, nylon webbing, or an elastic belt. The present invention is not limited in any way. The body 10 has a length, a width, two opposite ends, a bottom face, a top face, an adhesive surface 11, and a mounting surface 12. The adhesive surface 11 and the mounting surface 12 are respectively disposed on the bottom face and the top face of the body 10 along a lengthwise direction of the body 10. The adhesive surface 11 is used to adhere to a patient's skin, so that the body 10 can be disposed at an injured part of the patient, and the at least one first supporting element 20 and the at least one second supporting element 30 are disposed on the mounting surface 12 of the body 10.

The at least one first supporting element 20 is disposed on the body 10 along the lengthwise direction of the body 10. In the present invention, there are multiple first supporting elements 20 disposed on the mounting surface 12 of the body 10 at spaced intervals along a width direction of the body 10. Each first supporting element 20 has a fixed segment 21, an engaging segment 22, a movable segment 23, and multiple supporting segments 24. The fixed segment 21 is securely disposed on the mounting surface 12 of the body 10 at one of the two opposite ends of the body 10 along the lengthwise direction of the body 10.

The engaging segment 22 is connected to the fixed segment 21, is a belt extending along the lengthwise direction of the body 10, and has a top face and multiple engaging units 25. The engaging units 25 are disposed on the top face of the engaging segment 22. The movable segment 23 is securely disposed on an end of the engaging segment 22 away from the fixed segment 21 above the mounting surface 12 of the body 10, and has a stuck unit 26. The multiple supporting segments 24 are securely disposed on the mounting surface 12 of the body 10 at spaced intervals between the fixed segment 21 and the movable segment 23, and each supporting segment 24 is movably connected to the engaging segment 22 to hold the engaging segment 22 steadily disposed above the mounting surface 12 of the body 10.

The at least one second supporting element 30 is disposed on the body 10 along the lengthwise direction of the body 10 and aligns with the at least one first supporting element 20. Preferably, in the present invention, there are multiple second supporting elements 30 disposed on the mounting surface 12 of the body 10 at spaced intervals along the width direction of the body 10. Each second supporting element 30 is connected to and aligns with a respective one of the multiple first supporting elements 20. That is, each second supporting element 30 is connected to a first supporting element 20 along the lengthwise direction of the body 10, and has a fixed segment 31, an engaging segment 32, a movable segment 33, and multiple supporting segments 34. The fixed segment 31 is securely disposed on the mounting surface 12 of the body 10 at the other one of the two opposite ends of the body 10 along the lengthwise direction of the body 10. Then the fixed segment 31 of the at least one second supporting element 30 and the fixed segment 21 of the at least one first supporting segment 20 are respectively disposed at the two opposite ends of the body 10 along the lengthwise direction of the body 10.

The engaging segment 32 is connected to the fixed segment 31, is a belt extending along the lengthwise direction of the body 10, and has a bottom face and multiple engaging units 35. The engaging units 35 are disposed on the bottom face of the engaging segment 32, and the stuck unit 26 of the movable segment 23 of the at least one first supporting element 20 engages with the engaging units 35 of the at least one second supporting element 30. The movable segment 33 is securely disposed on an end of the engaging segment 32 away from the fixed segment 31 above the mounting surface 12 of the body 10, and has a stuck unit 36 engaging with the engaging units 25 of the at least one first supporting element 20 as shown in FIG. 3. The multiple supporting segments 34 are securely disposed on the mounting surface 12 of the body 10 at spaced intervals between the fixed segment 31 and the movable segment 33, and each supporting segment 34 is movably connected to the engaging segment 32 to hold the engaging segment 32 steadily disposed above the mounting surface 12 of the body 10.

Figure 3A:
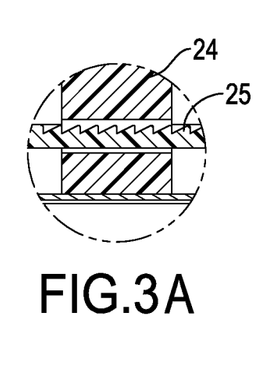
FIGS. 3A to 3D are enlarged and cross-sectional side views of the patch with an expansion support effect in FIG. 3.
Figure 3B:
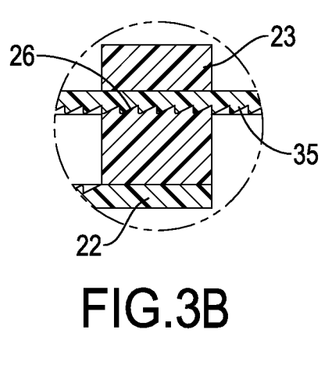
Figure 3C:
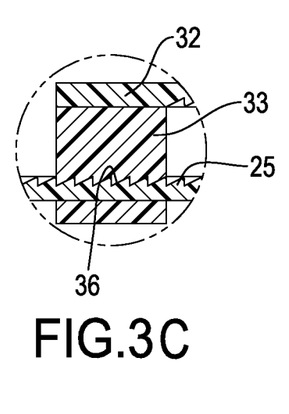
Figure 3D:
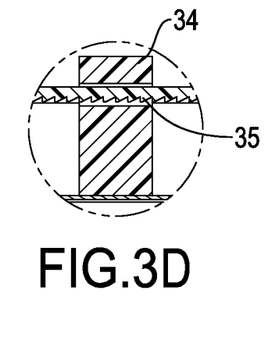

Preferably, in the first embodiment of the present invention, the fixed segment 21, 31 of each supporting element 20, 30 is a block securely disposed on the body 10, the movable segment 23, 33 is a block securely connected to a respective one of the engaging segments 22, 32, and each supporting segment 24, 34 is a block mounted with a respective one of the engaging segments 22, 32. Each said block is disposed on the mounting surface 12 of the body 10 by an injection molding method. Furthermore, with reference to FIGS. 3B and 3C, each engaging unit 25, 35 is a one-way engaging tooth, and each stuck unit 26, 36 is an engaging hole formed through the respective one of the movable segments 23, 33. In addition, with reference to FIGS. 3A and 3D, each supporting segment 24, 34 has a through hole formed through the supporting segment 24, 34 to connect with the respective one of the engaging units 25, 35.

Figure 4:
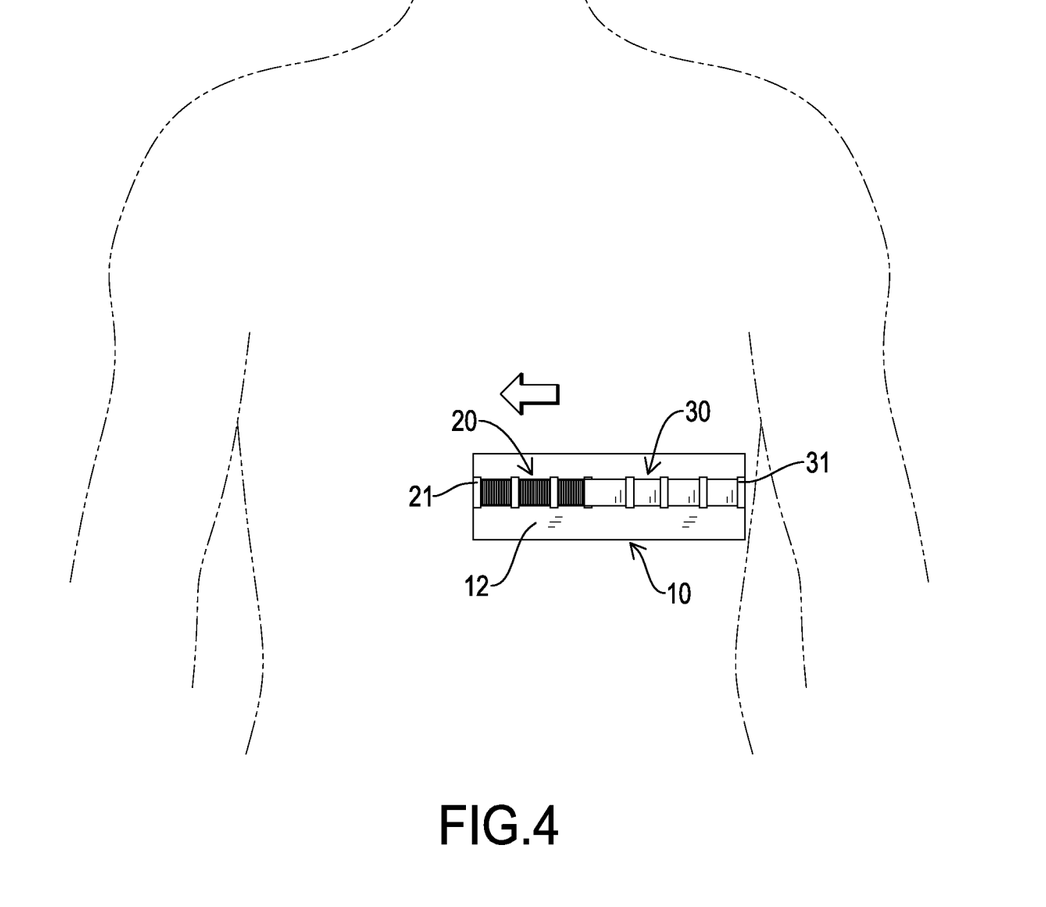
FIG. 4 is a schematic side view of the patch with an expansion support effect in FIG. 1, showing the patch with an expansion support effect worn on a patient.
Figure 5:
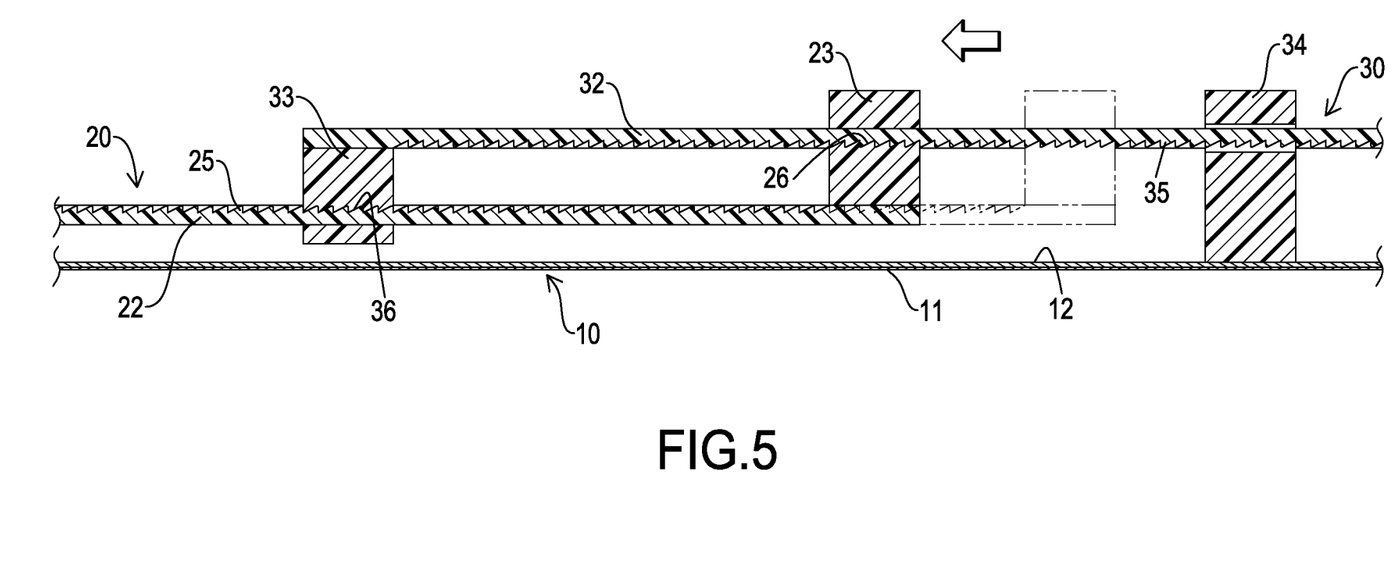
FIG. 5 is an enlarged and operational side view of the patch with an expansion support effect in FIG. 1.

With reference to FIGS. 4 and 5, when the first embodiment of the patch with an expansion support effect of the present invention is in use, a user cuts the body 10 into a size according to the size and scope of a patient's rib injury site, and pulls one or two of the opposite ends of the body 10 to expand the body 10 along the lengthwise direction of the body 10 to make the body 10 expand and deform along the lengthwise direction of the body 10. When the body 10 is expanded to a desired size for the patient's rib injury site, the adhesive surface 11 of the body 10 is adhered to two sides of the patient's rib injury site. During the expansion deformation of the body 10, the fixed segments 21, 31 of the two supporting elements 20, 30 are securely disposed on the mounting surface 12 of the body 10, and the two supporting elements 20, 30 are moved with each other when the body 10 is stretched and deformed by an external force.

After the body 10 expands and deforms, the two supporting elements 20, 30 can be stably positioned on the body 10 after mutual activities by an engagement between the engaging units 25, 35 of the engaging segment 22, 32 of each supporting element 20, 30 and the stuck unit 26, 36 of the movable segment 22, 32 of the other one of the supporting elements 20, 30. Then, the structural strength provided by the two supporting elements 20, 30 after the engagement can be provided to the expanded and deformed body 10 to have a support effect with a certain strength, thereby providing the support effect to the patch. Additionally, the supporting segments 24, 34 of each supporting element 20, 30 can also provide further assistant support effects, so that the patch can fully match the condition of the patient's rib fracture site, and safely and properly complete the fixation of the rib fracture site. The patch not only has relatively simplified structure and is easy to operate, but also provides a certain degree of expansion support effect.

Figure 6:
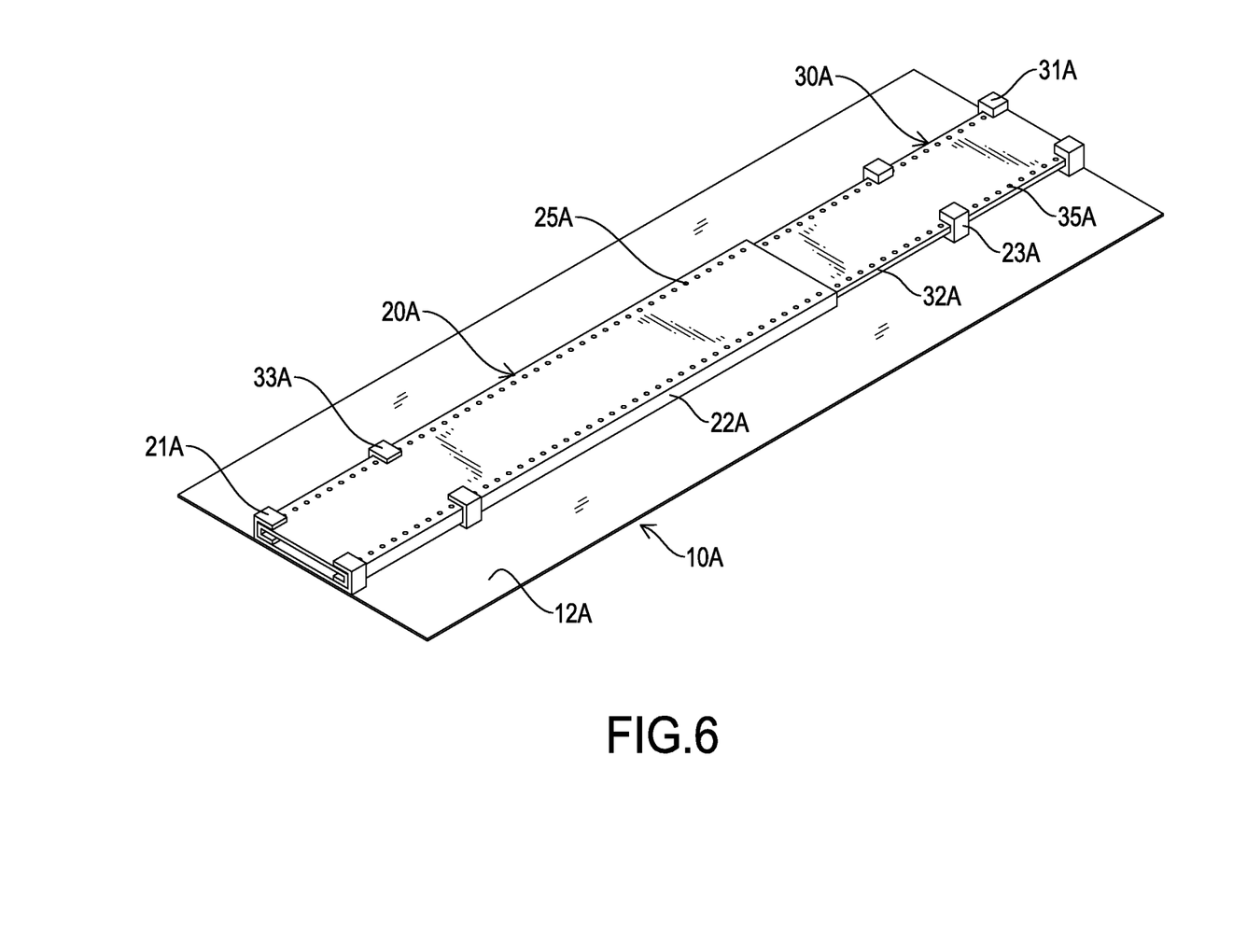
FIG. 6 is a perspective view of a second embodiment of a patch with an expansion support effect in accordance with the present invention.
Figure 7:
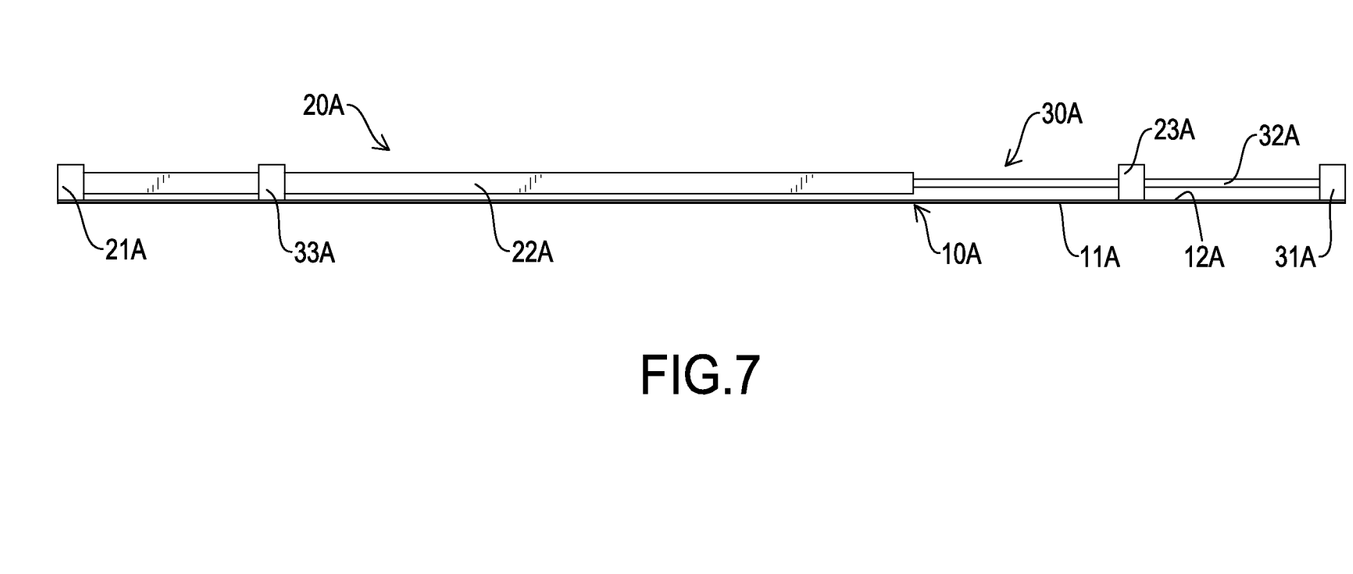
FIG. 7 is a side view of the patch with an expansion support effect in FIG. 6.
Figure 8:
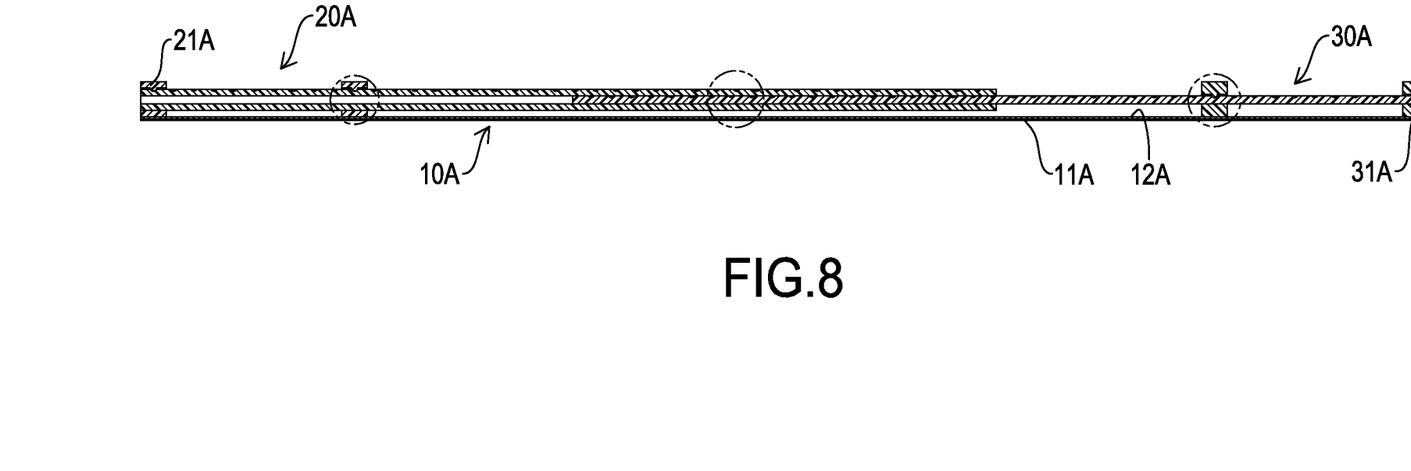
FIG. 8 is a cross-sectional side view of the patch with an expansion support effect in FIG. 6.

With reference to FIGS. 6 to 8, a second embodiment of a patch with an expansion support effect in accordance with the present invention is substantially the same as the first embodiment as shown in FIGS. 1 to 3 except for the following features. The engaging segment 22A of the at least one first supporting element 20A is an inverted U-shaped rail, the engaging segment 32A of the at least one second supporting element 30A is a plate mounted with the rail, and the two supporting elements 20, 30 can be moved with each other. Since the two supporting elements 20A, 30A are a structural form of rail and plate and have certain structural strength, in the second embodiment of the present invention, each supporting element 20A, 30A is not provided with the multiple supporting segments 24, 34. Further, the fixed segments 21A, 31A of the two supporting elements 20A, 30A are respectively disposed on the opposite ends of the body 10A in the lengthwise direction of the body 10A, the movable segment 23A of the at least one first supporting member 20A is securely disposed on the mounting surface 12A of the body 10A adjacent to the fixed segment 31A of the at least one second supporting element 30A, and the movable segment 33A of the at least one second supporting member 30A is securely disposed on the mounting surface 12A of the body 10A adjacent to the fixed segment 21A of the at least one first supporting element 30A.

Figure 8A:
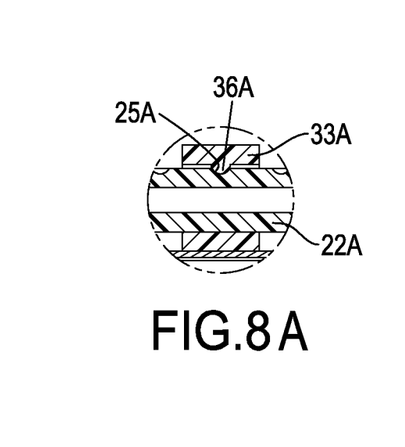
FIGS. 8A to 8C are enlarged and cross-sectional side views of the patch with an expansion support effect in FIG. 8.
Figure 8B:
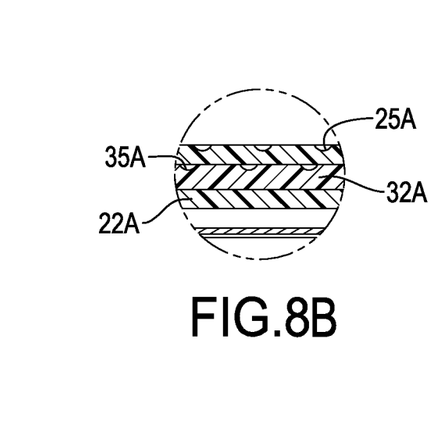
Figure 8C:
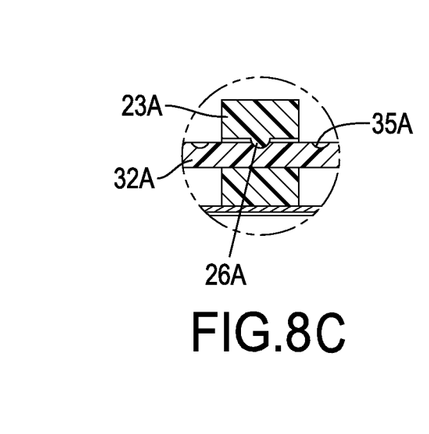

With reference to FIG. 8B, the multiple engaging units 25A, 35A of the two supporting elements 20A, 30A are respectively provided on the corresponding engaging segments 22A, 32A, and each engaging unit 25A, 35A is an engaging recess formed in the top face of the corresponding engaging segment 22A, 32A. Preferably, the multiple engaging units 25A, 35A are arranged into two rows at linearly spaced intervals on the top face of the corresponding engaging segment 22A, 32A along the lengthwise direction of the body 10A. Each movable segment 23A, 33A is a frame with an opening facing up and has two arms extended to the top face of the corresponding engaging segment 22A, 32A. With reference to FIGS. 8A and 8C, each arm has a stuck unit 26A, 36A protruded from a bottom of the corresponding arm. The stuck units 26A, 36A on the two arms of each movable segment 23A, 33A engage with two of the engaging units 25A, 35A of the corresponding engaging segment 22A, 32A. That is, the two stuck units 26A of the movable segment 23A of the at least one first supporting element 20A engage with two of the engaging units 35A of the engaging segment 35A of the at least one second supporting element 30A, and the two stuck units 36A of the movable segment 33A of the at least one second supporting element 30A engage with two of the engaging units 25A of the engaging segment 25A of the at least one first supporting element 20A. Preferably, each stuck unit 26A, 36A is an engaging bead.

Figure 9:
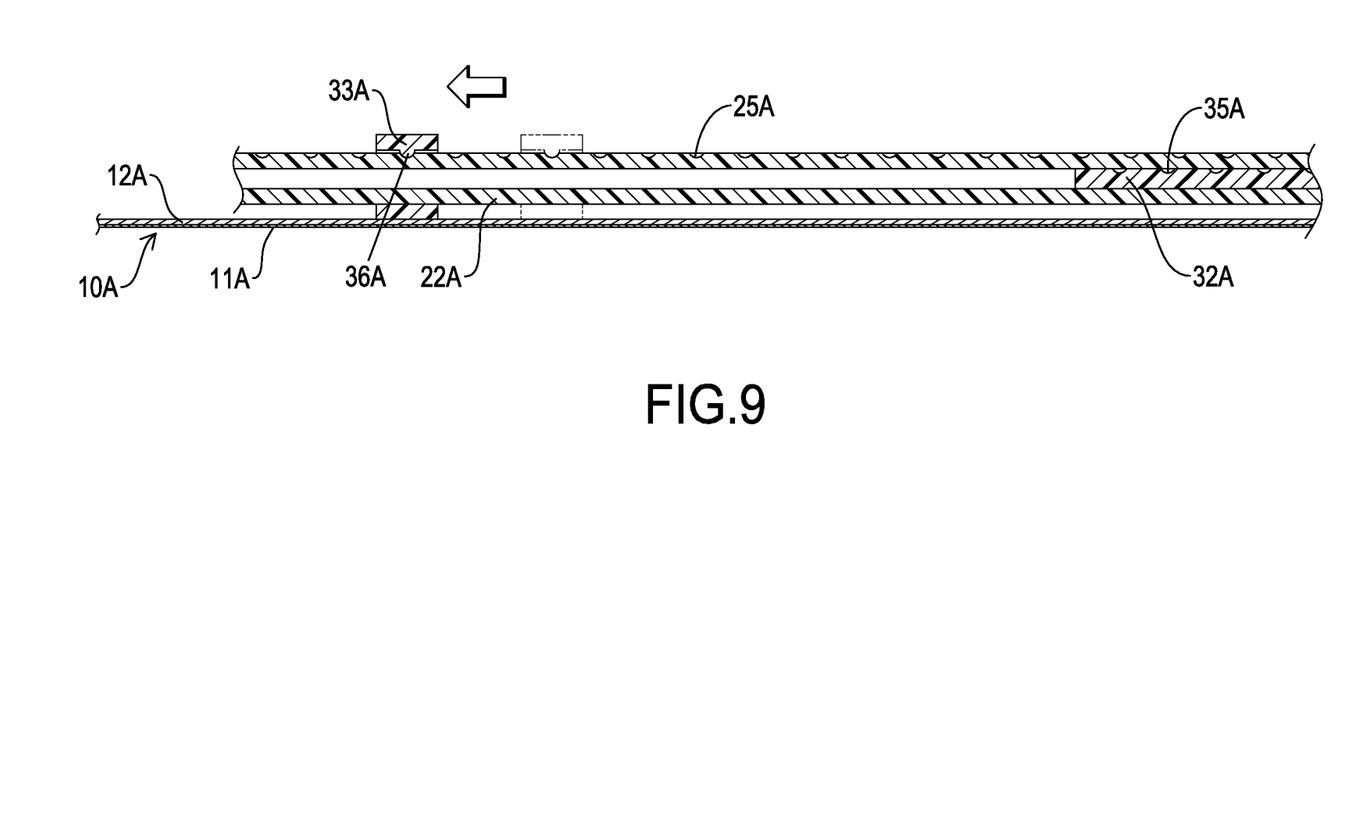
FIG. 9 is an enlarged and operational side view of the patch with an expansion support effect in FIG. 6.

With reference to FIG. 9, to use the second embodiment of the patch with an expansion support effect of the present invention, cut the body 10A into a size according to the size and scope of the patient's rib injury site, and pull one or two of the opposite ends of the body 10A to expand the body 10A along the lengthwise direction of the body 10A to make the body 10A expand and deform along the lengthwise direction of the body 10A. When the body 10A is expanded to a desired size for the patient's rib injury site, the adhesive surface 11A of the body 10A is adhered to two sides of the patient's rib injury site. During the expansion deformation of the body 10A, the fixed segments 21A, 31A of the two supporting elements 20A, 30A are securely disposed on the mounting surface 12A of the body 10A, and the rail and plate of the two supporting elements 20A, 30A are moved with each other when the body 10A is stretched and deformed by an external force.

After the body 10A expands and deforms, the two supporting elements 20A, 30A can be stably positioned on the body 10A after mutual activities by an engagement between the engaging units 25A, 35A of the engaging segment 22A, 32A of each supporting element 20A, 30A and the stuck unit 26A, 36A of the movable segment 22A, 32A of the other one of the supporting elements 20A, 30A. Then, the structural strength provided by the two supporting elements 20A, 30A after the engagement can be provided to the expanded and deformed body 10A to have a support effect of a certain strength, thereby providing the support effect to the patch. Additionally, the supporting segments 24A, 34A of each supporting element 20A, 30A can also provide further assistant support effects, so that the patch can fully match the condition of the patient's rib fracture site, and safely and properly complete the fixation of the rib fracture site. The patch not only has the relatively simplified structure and is easy to operate, but also can provide a certain degree of expansion support effect.

Figure 10:
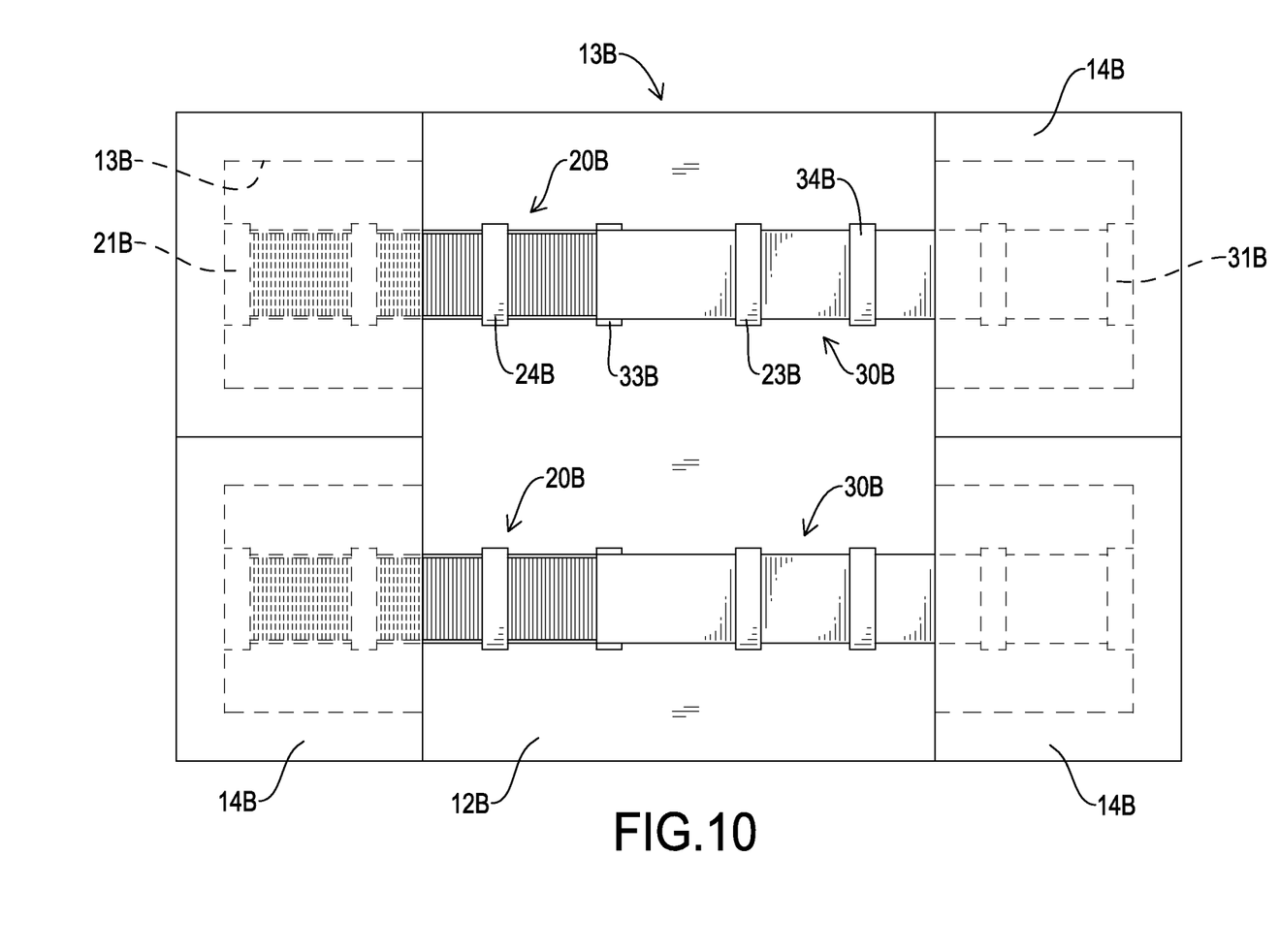
FIG. 10 is a side view of a third embodiment of a patch with an expansion support effect in accordance with the present invention.

With reference to FIG. 10, a third embodiment of a patch with an expansion support effect in accordance with the present invention is substantially the same as the first embodiment as shown in FIGS. 1 to 3 except for the following features. The body 10B has at least one receiving space 13B formed on the mounting surface 12B. The at least one receiving space 13B is formed on the mounting surface 12B of the body 10B by two covering sheets 14B respectively disposed on the mounting surface 12B at the two opposite ends of the body 10B. Each covering sheet 14B has an opening, and the openings of the two covering sheets 14B face to each other to form the at least one receiving space 13B between the two covering sheets 14B. The at least one first supporting element 20B is disposed in the at least one receiving space 13B of the body 10B without securely disposed on the mounting surface 12B of the body 10B. That is, the fixed segment 21B, the movable segment 23B, and the supporting segments 24B only abut the mounting surface 12B of the body 10B, and the fixed segment 21B of the at least one first supporting element 20B is restricted by one of the covering sheets 14B disposed on one of the two opposite ends of the body 10B and is not exposed outside the body 10B.

Similarly, the at least one second supporting element 30B is disposed in the at least one receiving space 13B of the body 10B, and is connected to the at least one first supporting element 20B without securely disposed on the mounting surface 12B of the body 10B. That is, the fixed segment 31B, the movable segment 33B, and the supporting segments 34B only abut the mounting surface 12B of the body 10B, and the fixed segment 31B of the at least one second supporting element 30B is restricted by the other one of the covering sheets 14B disposed on the other one of the two opposite ends of the body 10B and is not exposed outside the body 10B. Then the at least one first supporting element 20B and the at least one second supporting element 30B are disposed in the at least one receiving space 13B of the body 10B and are respectively restricted by the two covering sheets 14B.

Preferably, the body 10B has two receiving spaces 13B disposed on the mounting surface 12B at a spaced interval and parallel with each other. A pair of supporting elements 20B, 30B connected to each other is disposed in each one of the two receiving spaces 13B. The two pairs of supporting elements 20B, 30B respectively mounted in the two receiving spaces 13B are stretched and pushed against the two covering sheets 14B to provide a certain support strength to the expanded and deformed body 10B.

In summary, when the patch with an expansion support effect of the present invention is used, at least two of the supporting elements 20, 20A, 20B, 30, 30A, 30B are linearly arranged and moved with each other on the body 10, 10A, and the engagement is provided between the engaging units 25, 25A, 35, 35A and the stuck units 26, 26A, 36, 36A of each supporting element 20, 20A, 20B, 30, 30A, 30B. Then the expanded and deformed bodies 10, 10A, 10B can be provided with certain support strengths by the engagements between the two supporting elements 20, 20A, 20B, 30, 30A, 30B after the bodies 10, 10A, 10B are stretched and deformed by an external force, which not only simplifies the overall structural complexity and greatly reduces the required cost, but also cooperates with the elastic contraction tension of the body 10, 10A, 10B and the supporting force of the two supporting elements 20, 20A, 20B, 30, 30A, 30B. It can effectively avoid the pain caused by the patient during the moving activities, so as to provide a patch with a simple structure, convenient use, and an expansion support effect.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A patch with an expansion support effect comprising a body, at least one first supporting element, and at least one second supporting element, the at least one first supporting element and the at least one second supporting element disposed on the body, and the at least one second supporting element being mutually active and set up with the at least one first supporting element;

wherein the body is an elongated sheet and has a length, two opposite ends, a bottom face, a top face, an adhesive surface, and a mounting surface, the adhesive surface and the mounting surface are respectively disposed on the bottom face and the top face of the body along a lengthwise direction of the body;

wherein the at least one first supporting element is disposed on the body along the lengthwise direction of the body and has a fixed segment, an engaging segment, and a movable segment, the fixed segment is disposed on the mounting surface of the body at one of the two opposite ends of the body along the lengthwise direction of the body, the engaging segment is connected to the fixed segment, and the movable segment is disposed on the mounting surface of the body away from the fixed segment;

wherein the at least one second supporting element is disposed on the body along the lengthwise direction of the body, aligns with the at least one first supporting element, and has a fixed segment disposed on the mounting surface of the body at the other one of the two opposite ends of the body along the lengthwise direction of the body, an engaging segment connected to the fixed segment of the at least one second supporting element, and a movable segment disposed on the mounting surface of the body away from the fixed segment of the at least one second supporting element; and the engaging segment of each one of the at least one first supporting element and the at least one second supporting element engages with the movable segment of the other one of the at least one first supporting element and the at least one second supporting element; wherein the engaging segment of the at least one first supporting element has multiple engaging units; the movable segment of the at least one second supporting element has at least one stuck unit; and the at least one stuck unit of the movable segment of the at least one second supporting element engages with the engaging units of the engaging segment of the at least one first supporting element; wherein each engaging unit of each one of the at least one first supporting element and the at least one second supporting element is a one-way engaging tooth; the at least one stuck unit of each one of the at least one first supporting element and the at least one second supporting element is an engaging hole formed through the respective movable segment; and an engagement between the one-way engaging tooth and the engaging hole of the at least one first supporting element and the at least one second supporting element allows adjusting a distance between the at least one first supporting element and the at least one second supporting element; wherein the engaging segment of each one of the at least one first supporting element and the at least one second supporting element is a belt extending along the lengthwise direction of the body; and the movable segment of each one of the at least one first supporting element and the at least one second supporting element is securely disposed on an end of the engaging segment of the respective supporting element away from the fixed segment of the respective supporting element and is disposed above the mounting surface of the body and wherein each one of the at least one first supporting element and the at least one second supporting element has multiple supporting segments securely disposed on the mounting surface of the body at spaced intervals between the fixed segment and the movable segment of the respective supporting element; and each supporting segment of each one of the at least one first supporting element and the at least one second supporting element is movably connected to the engaging segment of the respective supporting element to hold the engaging segment of the respective supporting element steadily disposed above the mounting surface of the body.

2. The patch with an expansion support effect as claimed in claim 1, wherein the engaging segment of the at least one second supporting element has multiple engaging units;

the movable segment of the at least one first supporting element has at least one stuck unit; and the at least one stuck unit of the movable segment of the at least one first supporting element engages with the engaging units of the engaging segment of the at least one second supporting element.

3. The patch with an expansion support effect as claimed in claim 1, wherein each supporting segment has a through hole formed through the supporting segment to connect with the respective engaging unit.

4. The patch with an expansion support effect as claimed in claim 3, wherein the patch has multiple first supporting elements disposed on the mounting surface of the body at spaced intervals along a width direction of the body;

the patch has multiple second supporting elements disposed on the mounting surface of the body at spaced intervals along the width direction of the body; and each one of the multiple second supporting elements is connected to and aligns with a respective one of the multiple first supporting elements along the lengthwise direction of the body.

5. The patch with an expansion support effect as claimed in claim 1, or 2, wherein each one of the at least one first supporting element and the at least one second supporting element has multiple supporting segments securely disposed on the mounting surface of the body at spaced intervals between the fixed segment and the movable segment of the respective supporting element; and each supporting segment of each one of the at least one first supporting element and the at least one second supporting element is movably connected to the engaging segment of the respective supporting element to hold the engaging segment of the respective supporting element steadily disposed above the mounting surface of the body.

6. The patch with an expansion support effect as claimed in claim 1, or 2, wherein the patch has multiple first supporting elements disposed on the mounting surface of the body at spaced intervals along a width direction of the body;

the patch has multiple second supporting elements disposed on the mounting surface of the body at spaced intervals along the width direction of the body; and each one of the multiple second supporting elements is connected to and aligns with a respective one of the multiple first supporting elements along the lengthwise direction of the body.

7. The patch with an expansion support effect as claimed in claim 1 or 2, wherein the engaging segment of the at least one first supporting element is a rail; and the engaging segment of the at least one second supporting element is a plate mounted with the rail to enable the at least one second supporting element to move with the at least one first supporting element.

8. The patch with an expansion support effect as claimed in claim 7, wherein the fixed segments of the at least one first supporting element and the at least one second supporting element are respectively disposed on the two opposite ends of the body along the lengthwise direction of the body;

the movable segment of the at least one first supporting element is securely disposed on the mounting surface of the body adjacent to the fixed segment of the at least one second supporting element; and the movable segment of the at least one second supporting element is securely disposed on the mounting surface of the body adjacent to the fixed segment of the at least one first supporting element.

9. The patch with an expansion support effect as claimed in claim 8, wherein the multiple engaging units of each one of the at least one first supporting element and the at least one second supporting element are arranged into two rows at linearly spaced intervals on a top face of the respective engaging segment along the lengthwise direction of the body;

the movable segment of each one of the at least one first supporting element and the at least one second supporting element is a frame with an opening facing up and has two arms extended to the top face of the respective engaging segment, and each arm has a stuck unit protruded from a bottom of the arm; and the stuck units on the two arms of the movable segment of each one of the at least one first supporting element and the at least one second supporting element engage with two of the engaging units of the corresponding engaging segment.

10. The patch with an expansion support effect as claimed in claim 9, wherein each engaging unit is an engaging recess formed in the top face of the corresponding engaging segment; and each stuck unit is an engaging bead.

11. The patch with an expansion support effect as claimed in claim 10, wherein the patch has multiple first supporting elements disposed on the mounting surface of the body at spaced intervals along a width direction of the body;

the patch has multiple second supporting elements disposed on the mounting surface of the body the at spaced intervals along a width direction of the body; and each one of the multiple second supporting elements is connected to and aligns with a respective one of the multiple first supporting elements along the lengthwise direction of the body.

12. The patch with an expansion support effect as claimed in claim 9, wherein the patch has multiple first supporting elements disposed on the mounting surface of the body at spaced intervals along a width direction of the body;

the patch has multiple second supporting elements disposed on the mounting surface of the body at spaced intervals along a width direction of the body; and each one of the multiple second supporting elements is connected to and aligns with a respective one of the multiple first supporting elements along the lengthwise direction of the body.

13. The patch with an expansion support effect as claimed in claim 7, wherein the multiple engaging units of each one of the at least one first supporting element and the at least one second supporting element are arranged into two rows at linearly spaced intervals on a top face of the respective engaging segment along the lengthwise direction of the body;

the movable segment of each one of the at least one first supporting element and the at least one second supporting element is a frame with an opening facing up and has two arms extended to the top face of the respective engaging segment, and each arm has a stuck unit protruded from a bottom of the arm; and the stuck units on the two arms of the movable segment of each one of the at least one first supporting element and the at least one second supporting element engage with two of the engaging units of the engaging segment.

14. The patch with an expansion support effect as claimed in claim 13, wherein the patch has multiple first supporting elements disposed on the mounting surface of the body at spaced intervals along a width direction of the body;

the patch has multiple second supporting elements disposed on the mounting surface of the body at spaced intervals along a width direction of the body; and each one of the multiple second supporting elements is connected to and aligns with a respective one of the multiple first supporting elements along the lengthwise direction of the body.

15. The patch with an expansion support effect as claimed in claim 1, or 2, wherein the body has at least one receiving space formed on the mounting surface;

the at least one first supporting element is disposed in the at least one receiving space of the body;

the fixed segment, the movable segment, and the supporting segments of the at least one first supporting element abut the mounting surface of the body;

the at least one second supporting element is disposed in the at least one receiving space of the body; and the fixed segment, the movable segment, and the supporting segments of the at least one second supporting element abut the mounting surface of the body.

16. The patch with an expansion support effect as claimed in claim 15, wherein the at least one receiving space of the body is formed on the mounting surface of the body by two covering sheets respectively disposed on the mounting surface at the two opposite ends of the body;

each covering sheet has an opening, and the openings of the two covering sheets face to each other to form the at least one receiving space between the two covering sheets;

the fixed segment of the at least one first supporting element is restricted by one of the covering sheets disposed on one of the two opposite ends of the body without exposed outside the body; and the fixed segment of the at least one second supporting element is restricted by the other one of the covering sheets disposed on the other one of the two opposite ends of the body without exposed outside the body.

* * * * *